US007615525B2

United States Patent
Goeke

(10) Patent No.: US 7,615,525 B2
(45) Date of Patent: Nov. 10, 2009

(54) DIOXA-TRICYCLOUNDECANE COMPOUNDS

(75) Inventor: Andreas Goeke, Shanghai (CN)

(73) Assignee: Givaudan Schweiz AG, Vernier (CH)

( * ) Notice: Subject to any disclaimer, the term of this patent is extended or adjusted under 35 U.S.C. 154(b) by 160 days.

(21) Appl. No.: 11/720,661

(22) PCT Filed: Nov. 30, 2005

(86) PCT No.: PCT/CH2005/000715

§ 371 (c)(1),
(2), (4) Date: Oct. 12, 2007

(87) PCT Pub. No.: WO2006/058450

PCT Pub. Date: Jun. 8, 2006

(65) Prior Publication Data

US 2008/0207482 A1    Aug. 28, 2008

(51) Int. Cl.
*A61K 8/33* (2006.01)
*C07D 317/70* (2006.01)
(52) U.S. Cl. ............................ 512/12; 512/13; 549/433
(58) Field of Classification Search ............ 512/12, 512/13; 549/433
See application file for complete search history.

(56) References Cited

U.S. PATENT DOCUMENTS 5,892,062 A * 4/1999 Pickenhagen et al. ....... 549/432

FOREIGN PATENT DOCUMENTS

| EP | 857723 A1 | 8/1998 |
| EP | 1234822 A1 | 8/2002 |
| EP | 1496055 A1 | 1/2005 |

OTHER PUBLICATIONS

International Search Report dated Jun. 27, 2006 for Application PCT/CH2005/000715.
Written Opinion of the International Searching Authority for Application PCT/CH2005/000715, Jun. 27, 2006.
English-language abstract for EP 857723 obtained online from esp@cenet, 1998.

* cited by examiner

*Primary Examiner*—Mark Eashoo
*Assistant Examiner*—Peter F Godenschwager

(57) ABSTRACT

A compound of the formula I

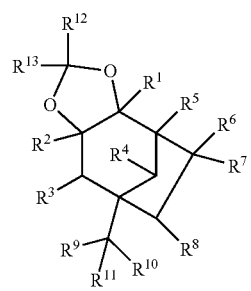

in which the moieties $R^1$-$R^{13}$ are independently selected from the following moieties:
$R^1$, $R^5$, $R^6$, $R^8$, $R^{11}$—H, methyl, ethyl, propyl, isopropyl; $R^3$—H, methyl, ethyl, propyl, isopropyl, vinyl; $R^4$—H, methyl, ethyl; $R^2$, $R^7$, $R^9$—H, methyl, ethyl, propyl, isopropyl, n-butyl, isobutyl, t-butyl; $R^{10}$—H, methyl, ethyl, propyl, isopropyl, t-butyl; $R^{12}$, $R^{13}$—H, $C_{1-6}$ linear or branched alkyl; or $R^4$ and $R^{11}$ together with the carbon atoms to which they are attached form a 5- or a 6-membered cycloalkyl ring; or $R^6$ and $R^7$ together with the carbon atoms to which they are attached form a cycloalkyl ring having 3, 4, 5 or 6 members. The compounds have strong odours and are useful in fragrances and fragrance applications.

9 Claims, No Drawings

DIOXA-TRICYCLOUNDECANE COMPOUNDS

This is an application filed under 35 USC 371 of PCT/CH2005/000715.

This invention relates to chemical compounds, and more particularly to chemical compounds having novel or enhanced odour properties, and to compositions including such compounds.

It has been found that certain dioxa-tricyclo-undecane compounds have desirable olfactory properties and can therefore be used in applications where such properties are desirable. The invention therefore provides a compound of the formula I

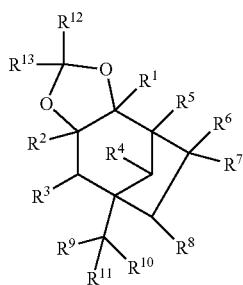

in which the moieties $R^1$-$R^{13}$ are independently selected from the following moieties:

$R^1$, $R^5$, $R^6$, $R^8$, $R^{11}$—H, methyl, ethyl, propyl, isopropyl;
$R^3$—H, methyl, ethyl, propyl, isopropyl, vinyl;
$R^4$—H, methyl, ethyl;
$R^2$, $R^7$, $R^9$—H, methyl, ethyl, propyl, isopropyl, n-butyl, isobutyl, t-butyl;
$R^{10}$—H, methyl, ethyl, propyl, isopropyl, t-butyl;
$R^{12}$, $R^{13}$—H, $C_{1-6}$ linear or branched alkyl;
or $R^4$ and $R^{11}$ together with the carbon atoms to which they are attached form a 5- or a 6-membered cycloalkyl ring;
or $R^6$ and $R^7$ together with the carbon atoms to which they are attached form a cycloalkyl ring having 3, 4, 5 or 6 members.

The definition hereinabove given encompasses all stereochemical forms of the compound. The compound hereinabove described may be a mixture of isomers, or, if desired, it may be resolved by known methods into individual isomers. However, as such resolution inevitably adds to the cost of the process and therefore of the final materials, it is preferred to use the compound as a mixture.

A preferred compound is 8-isopropyl-2,4,4,10,10-pentamethyl-3,5-dioxa-tricyclo[6.2.1.0$^{2,6}$]undecane.

The compounds of the invention may be prepared by known methods, starting from the known compounds II

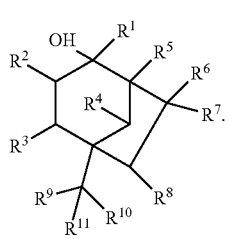

in which the moieties $R^1$-$R^{10}$ have the significances hereinabove defined.

The compounds of the invention have strong ambery woody and substantive odours and are useful in the preparation of fragrances and fragrance compositions. The invention therefore provides the use as a fragrance of a compound as hereinabove defined.

The invention further provides the use in a fragrance composition of a compound as hereinabove defined.

The compounds may be used in a broad range of fragrance applications, such as fine and functional fragrances, including perfumes, cosmetics, body care products and household products, for example, laundry, dishwashing and dishwasher products, polishes and cleaners, and so on. The invention therefore also provides a fragrance application comprising at least one compound as hereinabove defined.

The invention is further described with reference to the following non-limiting examples.

EXAMPLE 1

5-Isopropyl-2,7,7-trimethyl-bicyclo[3.2.1]oct-2-ene

A solution of 5-isopropyl-7,7-dimethyl-bicyclo[3.2.1]octan-2-ol (18.5 g, 88 mmol) and KHSO$_4$ (100 mg) in toluene (250 ml) was heated 36 h in a Dean-Stark apparatus. The solution was cooled and washed once with water and brine, dried (MgSO$_4$) and concentrated in vacuo to yield 5-isopropyl-2,7,7-trimethyl-bicyclo[3.2.1]oct-2-ene (13.77 g, 81%). $^{13}$H-NMR (100 MHz, CDCl$_3$): 140.4 (s), 118.7 (d), 52.1 (d), 51.5 (t), 46.1 (s), 46.0 (s), 39.1 (t), 37.6 (d), 37.4 (t), 31.5 (q), 26.9 (q), 24.6 (q), 18.2 (q), 18.0 (q) ppm. GC/MS (EI): 192 (M$^+$, 17), 177 (4), 149 (22), 136 (21), 121 (15), 107 (18), 93 (100), 77 (28), 57 (17), 41 (23). IR (ATR): 2957 s, 2933 s, 2869 m, 1468 m, 1452 m, 1366 m cm$^{-1}$.

8-Isopropyl-2,4,4,10,10-pentamethyl-3,5-dioxa-tricyclo[6.2.1.0$^{2,6}$]undecane

A solution of 5-isopropyl-2,7,7-trimethyl-bicyclo[3.2.1]oct-2-ene (1.00 g, 5.2 mmol), OsO$_4$ (0.052 mmol, 2.5% in t-BuOH) and N-morpholine-N-oxide (913.3 mg, 6.76 mmol) in aqueous acetone (10 ml) was stirred at room temperature for 40 h. The mixture was diluted with MTBE, filtered, concentrated in vacuo and the residue purified by chromatography on silica (hexane:ethyl acetate=7:3). To the resulting diol (0.4 g) was added 2,2-dimethoxy-propane (5 ml) and a catalytic amount of p-TsOH and the solution was stirred for 5 h at room temperature. The mixture was now concentrated and the residue purified by chromatography on silica (hexane:ethyl acetate=95:5) to yield a colorless oil (0.41 g, 30%). $^1$H-NMR (400 MHz, CDCl$_3$): 4.12 (dd, J=8.9 Hz, 8.5 Hz, 1H, 6-H), 2.09 (dd, J=12.0 Hz, 2.1 Hz, 1H, 11-H$_a$), 1.84 (d, J=5.1 Hz, 1H, 1-H), 1.80 (ddd, J=14.2 Hz, 8.9 Hz, 2.5 Hz, 1H, 7-H$_a$), 1.62 (ddd, J=14.2 Hz, 6.1 Hz, 2.1 Hz, 1H, 7-H$_b$), 1.53-1.48 (m, 1H, 11-H$_b$), 1.52 (s, 3H), 1.48 (s, 6H), 1.46 (sept., J=6.8 Hz, 1H, 8-CH(CH$_3$)$_2$), 1.38 (dd, J=13.2 Hz, 2.0 Hz, 1H, 9-H$_a$), 1.26 (dd, J=13.2 Hz, 2.0 Hz, 1H, 9-H$_b$), 1.16 (s, 3H), 1.10 (s, 3H), 0.86 (d, J=6.8 Hz, 3H, 8-CH(CH$_3$)$_a$), 0.80 (d, J=6.8 Hz, 3H, 8-CH(CH$_3$)$_b$) ppm. $^{13}$H-NM (100 MHz, CDCl$_3$): 108.6 (s), 84.6 (s), 78.2 (d), 54.3 (d), 52.4 (t), 45.7 (s), 39.4 (s), 38.1 (t), 37.7 (d), 36.1 (t), 35.1 (q), 30.4 (q), 29.7 (q), 29.4 (q), 27.6 (q), 18.2 (q), 17.9 (q) ppm. GC/MS (EI): 266 (M$^+$, 1), 251 (14), 209 (46), 165 (98), 137 (67), 109 (31), 95 (52), 81 (42), 69 (36), 55 (39), 43 (100), 41 (49). IR (ATR): 2958 m, 2873 m, 1466 m, 1366 m, 1229 s, 1207 m, 1074 s, 1049 m, 1014 m cm$^{-1}$.

EXAMPLE 2

The following compounds were prepared according to example 1.

5-sec-Butyl-2,7,7-trimethyl-bicyclo[3.2.1]oct-2-ene

Mixture of 2 diastereomers: $^{13}$H-NMR (100 MHz, CDCl$_3$): 140.4 (2 s), 118.7, 118.6 (d), 52.7, 52.3 (t), 52.0, 51.9 (d), 46.7, 46.6 (s), 45.9, 45.8 (s), 45.8, 45.5 (d), 39.5, 39.3 (t), 37.6, 37.0 (t), 31.6, 31.5 (q), 26.9 (2 q), 24.9, 24.8 (t), 24.6 (2 q), 14.2, 14.1 (q), 18.0, 12.9 (q) ppm. GC/MS (EI): 206 (M$^+$, 14), 177 (4), 149 (38), 135 (4), 121 (24), 107 (19), 93 (100), 77 (18), 57 (35), 41 (17). IR (ATR): 2959 s, 2930 s, 2866 m, 1451 m, 1378 m, 884 m cm$^{-1}$.

8-sec-Butyl-2,4,4,10,10-pentamethyl-3,5-dioxa-tricyclo[6.2.1.0$^{2,6}$]undecane

Mixture of 2 diastereomers (in a ratio of 1:1): $^1$H-NMR (400 MHz, CDCl$_3$): 4.10 (ddd, J=2.5, 6.2, 8.7 Hz, 1H), 2.18-2.11 (m, 1H), 1.85-1.81 (m, 1H), 1.79-1.26 (m, 6H), 1.52 (s, 3H), 1.48 (s, 6H), 1.15 (s, 3H), 1.10 (s, 3H), 0.88 (t, J=7.4 Hz, 3H), 0.85, 0.78 (2 d, J=6.8 Hz, 3H) ppm. $^{13}$H-NMR (100 MHz, CDCl$_3$): 108.6 (2 s), 84.6 (2 s), 78.2 (2 s), 54.2, 54.1 (d), 53.3, 53.1 (t), 46.2 (2 s), 45.9 (d), 45.6 (d), 39.4, 39.2 (s), 38.3, 38.1 (t), 36.4, 36.2 (t), 35.1 (2 q), 30.4 (2 q), 29.7 (2 q), 29.4 (2 q), 27.6 (2 q), 24.9, 24.8 (t), 14.3, 14.0 (q), 13.0, 12.8 (q) ppm. GC/MS (EI): 280 (M$^+$, 2), 265 (35), 223 (96), 165 (31), 151 (100), 109 (24), 95 (33), 81 (18), 57 (33), 43 (35).

The invention claimed is:

1. A compound of the formula I

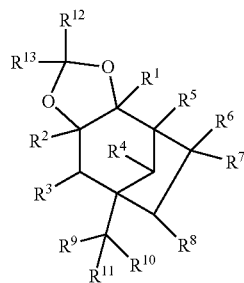

in which the moieties $R^1$-$R^{13}$ are independently selected from the following moieties:

$R^1$, $R^5$, $R^6$, $R^8$, $R^{11}$—H, methyl, ethyl, propyl, isopropyl;

$R^3$—H, methyl, ethyl, propyl, isopropyl, vinyl;

$R^4$—H, methyl, ethyl;

$R^2$, $R^7$, $R^9$—H, methyl, ethyl, propyl, isopropyl, n-butyl, isobutyl, t-butyl;

$R^{10}$—H, methyl, ethyl, propyl, isopropyl, t-butyl;

$R^{12}$, $R^{13}$—H, $C_{1-6}$ linear or branched alkyl;

or $R^4$ and $R^{11}$ together with the carbon atoms to which they are attached form a 5- or a 6-membered cycloalkyl ring;

or $R^6$ and $R^7$ together with the carbon atoms to which they are attached form a cycloalkyl ring having 3, 4, 5 or 6 members.

2. 8-isopropyl-2,4,4,10,10-pentamethyl-3,5-dioxa-tricyclo[6.2.1.0$^{2,6}$]undecane.

3. A fragrant compound according to claim 1.

4. A fragrance composition comprising a compound according to claim 1.

5. A fragrance application comprising at least one compound according to claim 1.

6. A fragrance application according to claim 5 wherein the fragrance application is selected from the group consisting of: fine fragrances, functional fragrances, perfumes, cosmetics, body care products, household products, laundry products, dishwashing products, dishwasher products, polishes and cleaners.

7. A fragrance application according to claim 6 wherein the fragrance application is selected from the group consisting of: fine fragrances, perfumes, cosmetics and body care products.

8. A fragrance application according to claim 6 wherein the fragrance application is selected from the group consisting of: household products, laundry products, dishwashing products, dishwasher products, polishes and cleaners.

9. A fragrance composition comprising 8-isopropyl-2,4,4,10,10-pentamethyl-3,5-dioxa-tricyclo[6.2.1.0$^{2,6}$]undecane.

* * * * *